United States Patent

Klauke

[11] 4,079,089
[45] Mar. 14, 1978

[54] FLUORINATION OF TRICHLOROMETHYL GROUPS

[75] Inventor: Erich Klauke, Odenthal, Germany

[73] Assignee: Bayer Aktiengesellschaft, Leverkusen, Germany

[21] Appl. No.: 731,475

[22] Filed: Oct. 12, 1976

[30] Foreign Application Priority Data

Oct. 17, 1975 Germany .............................. 2546532

[51] Int. Cl.$^2$ ............................................ C07C 25/14
[52] U.S. Cl. ................................................ 260/651 F
[58] Field of Search ..................................... 260/651 F

[56] References Cited

U.S. PATENT DOCUMENTS

| | | | |
|---|---|---|---|
| 1,967,244 | 8/1934 | Holt et al. ......................... | 260/651 F |
| 2,005,712 | 10/1935 | Holt et al. ......................... | 260/651 F |
| 3,258,500 | 6/1966 | Swamer et al. ................... | 260/651 F |
| 3,379,780 | 4/1968 | Robinson .......................... | 260/651 F |
| 3,457,310 | 7/1969 | Fischback ......................... | 260/651 F |
| 3,742,074 | 6/1973 | Hermann et al. ................. | 260/651 F |

FOREIGN PATENT DOCUMENTS

692,403 8/1964 Canada .............................. 260/651 F

*Primary Examiner*—Earl C. Thomas
*Assistant Examiner*—Wayne A. Langel
*Attorney, Agent, or Firm*—Burgess, Dinklage & Sprung

[57] ABSTRACT

A process for the preparation of a trichloromethyl-trifluoromethylbenzene of the formula

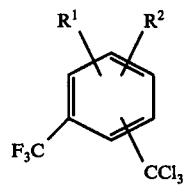

wherein $R^1$ and $R^2$ are independently selected from the group consisting of hydrogen, fluorine, chlorine and bromine which comprises contacting a bis-(trichloromethyl)-benzene of the formula

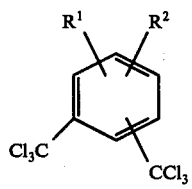

wherein $R^1$ and $R^2$ have the previously assigned significance with less than 6 mols of anhydrous hydrogen fluoride in the presence of a halogen transfer catalyst.

16 Claims, No Drawings

FLUORINATION OF TRICHLOROMETHYL GROUPS

The invention relates to a process for the preparation of trichloromethyl-trifluoromethyl-benzenes.

It is known from Z. obsc. chim. 37, 1626 (1967) to fluorinate the side chains in bis-(trichloromethyl)-benzene and subsequently to chlorinate one of the side chains again using aluminum chloride. This process is very involved and, because of the low selectivity of the chlorination reaction, leads to trichloromethyl-trifluoromethyl-benzenes in only small yields.

SUMMARY OF THE INVENTION

Broadly, this invention contemplates a method for the preparation of a trichloromethyl-trifluoromethyl-benzne of the formula

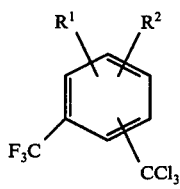

wherein $R^1$ and $R^2$ are independently selected from the group consisting of hydrogen, fluorine, chlorine and bromine which comprises contacting a bis-(trichloromethyl)-benzene of the formula

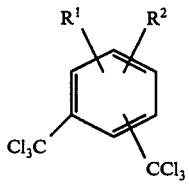

wherein $R^1$ and $R^2$ have the previously assigned significance with less than 6 mols of anhydrous hydrogen fluoride in the presence of a halogen transfer catalyst. Generally, the anhydrous hydrogen fluoride is present in at least a stoichiometric amount and up to but not including the 6 moles of anhydrous hydrogen fluoride.

A process for the preparation of trichloromethyl-trifluoromethyl-benzenes of the formula

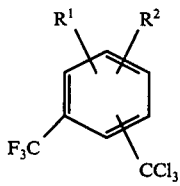

wherein $R^1$ and $R^2$ are identical or different and represent hydrogen, fluorine, chlorine or bromine, has been found which is characterized in that bis-(trichloromethyl)-benzenes of the formula

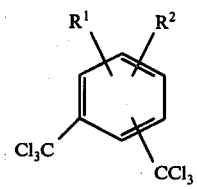

wherein $R^1$ and $R^2$ have the abovementioned meaning, are reacted with less than 6 mols of anhydrous hydrogen fluoride in the presence of a halogen transfer catalyst.

The process according to the invention can be illustrated by the following reaction equation for the reaction of bis-(trichloromethyl)-benzene with hydrogen fluoride.

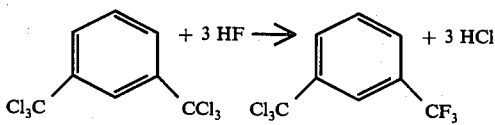

According to the process of the invention, anhydrous hydrogen fluoride is employed in an amount of less than 6 mols, generally in an amount of 0.5 to 5.0 mols, preferably of 1.5 to 3 mols and especially of 2.0 to 2.5 mols, per mol of bis-(trichloromethyl)-benzene.

The starting compounds for the process according to the invention are known (Houben-Weyl, volume V/3, 740 et seq. (1963). Examples which may be mentioned are: 1,3-bis-(trichloromethyl)-benzene, 1,4-bis-(trichloromethyl)-benzene, 2,4-bis-(trichloromethyl)-chlorobenzene, 2,6-bis-(trichloromethyl)-chlorobenzene, 2,4-bis-(trichloromethyl)-fluorobenzene, 2,6-bis-(trichloromethyl)-fluorobenzene, 3,5-bis-(trichloromethyl)-bromobenzene, 2,5-bis-(trichloromethyl)-chlorobenzene and 1,4-bis-(trichloromethyl-2,5-dichlorobenzene.

Halogen transfer catalysts are in themselves known (Houben-Weyl, volume V/3, 125 (1962)). Examples which may be mentioned are iron trichloride, titanium tetrachloride, aluminum chloride and antimony-V halides, such as antimony pentachloride, antimony pentafluoride and antimony-V chloride-fluoride, preferably antimony pentachloride.

In general, the catalysts are employed, for the process according to the invention, in amounts of 0.1 to 5 percent by weight and preferably of 0.5 to 3 percent by weight. Particularly preferentially, antimony pentachloride are used in amounts of 0.1 to 1 percent by weight and preferably of 0.25 to 0.75 percent by weight. It can be appropriate to add the total amount in two or more portions. In this case, it can furthermore be appropriate to add the second or subsequent portion in each case only after the evolution of hydrogen chloride has ceased or has subsided.

In general, the process according to the invention is carried out in the temperature range between the melting point and the boiling point of the starting compound, appropriately in the range from about 0° to about 150° C. Preferably, the reaction is carried out in the temperature range from 40° to 100° C, especially from 50° to 80° C.

The process according to the invention can be carried out under normal pressure and under excess pressure; in general, however, it is appropriate to carry out the reaction under excess pressure. The use of excess pressure is subject only to limits imposed by the apparatus. Appropriately, the reaction is carried out in the pressure range from 1 to 50 bars and preferably from 20 to 30 bars.

In general, the process according to the invention is carried out without using a solvent. However, under certain circumstances it can also be advantageous to carry out the reaction in the presence of a solvent or diluent; in this case all the solvents or diluents which are also suitable for carrying out Friedel-Crafts reactions can be employed. Preferred examples which may be mentioned are carbon disulphide and nitrobenzene.

The process according to the invention can be carried out, for example, in apparatuses which are not attacked by anhydrous hydrofluoric acid, hydrogen fluoride and/or hydrogen chloride.

When carrying out the process according to the invention, and especially when the reaction is carried out under excess pressure, it can be appropriate to work under a blanketing gas. Examples of blanketing gases which may be mentioned are hydrogen chloride, nitrogen and argon. In general, hydrogen chloride, which is necessarily obtained as a by-product during the reaction, is adequate as the blanketing gas. However, if the reaction mixture is not covered with hydrogen chloride, such as, for example, at the start of the reaction, other blanketing gases can advantageously be employed.

The process according to the invention can, for example, be carried out as follows:

Bis-(trichloromethyl)-benzene and the catalyst are initially introduced in a stirred autoclave and anhydrous hydrogen fluoride is added at about 0° to 5° C, whilst cooling. After closing the reactor vessel, a blanketing gas, for example nitrogen, is injected up to a slight excess pressure and the reaction mixture is warmed up to the reaction temperature. The hydrogen chloride liberated during the reaction is released, above the partial pressure of hydrogen fluoride, via a pressure valve and is removed. When the reaction has ended, the catalyst is precipitated by hydrolysis with water and filtered off. However, it is optionally also possible to separate off the catalyst, for example antimony pentachloride, by fractional distillation and to re-use it in the process according to the invention. Optionally, the catalyst can also be bound by means of an absorbent, for example active charcoal, silica gel, fuller's earth or zeolites, and then separated off by filtration.

The trifluoromethyl-trichloromethyl-benzene formed can, for example, be isolated, and purified, by fractional distillation.

It is surprising that trichloromethyl-trifluoromethyl-benzenes are formed selectively and in high yields from bis-(trichloromethyl)-benzenes by the process according to the invention, because it would have been expected that, even when less than 6 mols of hydrogen fluoride are used, chlorine would be replaced by fluorine in the two trichloromethyl groups simultaneously and, accordingly, a statistical distribution of the fluorine atoms on the two trihalogenomethyl groups would result. This is, as expected, indeed the case when bis-trichloromethyl-benzenes are reacted with anhydrous hydrogen fluoride without a catalyst.

The process according to the invention makes it possible to prepare trichloromethyl-trifluoromethyl-benzenes in a simple manner using the readily accessible bis-(trichloromethyl)-benzenes.

Compared with the known process (Z. obsc. chim. 37, 1626, (1967)), the process according to the invention has the following advantages:

The trichloromethyl-trifluoromethyl-benzenes are obtained in one process step. Since one trichloromethyl group is fluorinated preferentially, considerably less hydrogen fluoride is consumed. According to the known process the two trichloromethyl groups are first fluorinated and subsequently one of these groups is rechlorinated. With this process substantial amounts of the chlorinating agent and fluorinating agent are consumed unnecessarily.

The compounds prepared by the process according to the invention have a bactericidal and fungicidal action (U.S. Pat. No. 3,457,310). The compounds according to the invention can be reacted with benzene in the presence of aluminum chloride in 1 Friedel-Crafts-reaction to fungicides (DOS (German published specification) No. 17 95 249). Moreover they are intermediates for dyestuffs.

EXAMPLE 1

240 g of 1,3-bis-(trichloromethyl)-benzene and 2.4 g of iron-III chloride are initially introduced into an autoclave fitted with a stirrer, a reflux condenser, an off-gas line, leading from the top of the condenser through a pneumatically controlled pressure valve, a thermometer and a filler nozzle, which can be closed. 30 g of hydrogen fluoride (which corresponds to 2 mols of hydrogen fluoride per mol of bis-(trichloromethyl)-benzene) are then filled into the vessel, which is pre-cooled with ice/sodium chloride, and subsequently the mixture is covered, under a pressure of 2 bars, with nitrogen as the blanketing gas.

The mixture is warmed to the reaction temperature of 140° C, the pressure rising to 24 bars. When the temperature has risen to 50° C, stirring of the reaction mixture is started.

After 2 hours, the mixture is cooled, let down and filtered. The reaction mixture has the following composition according to gas chromatography:

a. 22.5% of 1,3-bis-(trichloromethyl)-benzene,
b. 7.1% of 1-trichloromethyl-3-(dichloro-fluoromethyl)-benzene,
c. 7.8% of 1-trichloromethyl-3-(chloro-difluoromethyl)-benzene,
d. 44.6% of 1-trichloromethyl-3-trifluoromethyl-benzene,
e. 1.22% of 1-(dichloro-fluoromethyl)-3-trifluoromethyl-benzene,
f. 4.7% of 1-(chloro-difluoromethyl)-3-trifluoromethyl-benzene and
g. 4.9% of 1,3-bis-(trifluoromethyl)-benzene.

88.5 g (which corresponds to a yield of 66%, based on the hydrogen fluoride employed) of 1-trichloromethyl-3-trifluoromethyl-benzene are obtained, in the temperature range of 88°–94° C and under 13 bars, by fractional distillation of the reaction mixture.

The individual components of the reaction mixture have the following physical constants: 1-trichloromethyl-3-(dichloro-fluoromethyl)-benzene, boiling point$_{30}$: 160° C; n$_D^{20}$: 1.5510, 1-trichloromethyl-3-(chloro-difluoromethyl)-benzene, boiling point$_{30}$: 135° C; n$_D^{20}$: 1.5207, 1-trichloromethyl-3-trifluoromethyl-benzene, boiling point$_{13}$: 90° C; n$_D^{20}$: 1.4888, 1-(dichloro-fluoromethyl)-3-trifluoromethyl-benzene, boiling point:

177° C; $n_D^{20}$: 1.4558 and 1-(chloro-difluoromethyl)-3-trifluoromethyl-benzene, boiling point: 146° C; $n_D^{20}$: 1.4182.

EXAMPLE 2

240 g of 1,3-bis-(trichloromethyl)-benzene and 2.4 g of antimony pentachloride are initially introduced into an autoclave fitted with a stirrer, a reflux condenser, an off-gas line, leading from the top of the condenser through a pneumatically controlled pressure valve, a thermometer and a filler nozzle, which can be closed. 15.5 g of anhydrous hydrogen fluoride are then added (this corresponds to approximately 1 mol of hydrogen fluoride per mol of bis-(trichloromethyl)-benzene) and the reaction mixture is covered, under a pressure of 2 bars, with nitrogen as the blanketing gas.

The mixture is warmed to a reaction temperature of 60° C, the pressure rising to 11.7 bars.

After 2 hours, the mixture is cooled and let down. The reaction product is washed, first with dilute hydrochloric acid and then with water, and is then dried. Analysis by gas chromatography gives the following composition:
a. 61.6% of 1,3-bis-(trichloromethyl)-benzene,
b. 4.6% of 1-trichloromethyl-3-(dichloro-fluoromethyl)-benzene,
c. 4.5% of 1-trichloromethyl-3-(chloro-difluoromethyl)-benzene,
d. 23.9% of trichloromethyl-3-trifluoromethyl-benzene,
e. 0.9% of 1-(dichloro-fluoromethyl)-3-trifluoromethyl-benzene,
f. 0.6% of 1-(chloro-difluoromethyl)-3-trifluoromethyl-benzene and
g. 0.3% of 1,3-bis-(trifluoromethyl)-benzene.

48 g (which corresponds to a yield of 67.3%, based on the hydrogen fluoride employed) of 1-trichloromethyl-3-trifluoromethyl-benzene are obtained by fractional distillation of the reaction mixture.

EXAMPLE 3

470 g of 1,3-bis-(trichloromethyl)-benzene, 1.2 g of antimony pentachloride and 75 g of anhydrous hydrogen fluoride are initially introduced into an autoclave. After closing the autoclave, nitrogen is introduced, as the blanketing gas, up to a pressure of 1.8 bars. The mixture is heated to 40° C; the hydrogen chloride pressure is kept at 25 bars by letting down occasionally by means of a valve. The mixture is stirred for 6 hours at 40° C.

After the end of the reaction, the mixture is cooled and let down. The reaction mixture is washed with dilute hydrochloric acid and then with water. 392 g of a reaction product, which is separated by fractional distillation, are obtained. 204 g (which corresponds to a yield of 61.8%, based on the hydrogen fluoride employed) of 1-trichloromethyl-3-trifluoromethyl-benzene are obtained.

Analysis of the reaction mixture by gas chromatography gives the following composition:
a. 25.8% of 1,3-bis-(trichloromethyl)-benzene,
b. 2.8% of 1-trichloromethyl-3-(dichloro-fluoromethyl)-benzene,
c. 3.7% of 1-trichloromethyl-3-(chloro-difluoromethyl)-benzene,
d. 54.4% of 1-trichloromethyl-3-trifluoromethyl-benzene,
e. 3.0% of 1-(dichloro-fluroomethyl)-3-trifluoromethyl-benzene,
f. 3.6% of 1-(chloro-difluoromethyl)-3-trifluoromethyl-benzene and
g. 4.7% of 1,3-bis-(trifluoromethyl)-benzene.

EXAMPLE 4

195 g of 1,3-bis-(trichloromethyl)-2-chlorobenzene, 1.9g of antimony pentachoride and 23 g of anhydrous hydrogen fluoride are initially introduced into an autoclave. The reaction mixture is stirred for 2 hours at 60° C.

After the end of the reaction, the mixture is cooled. The reaction mixture is washed with dilute hydrochloric acid and then with water. 176 g of the reaction product, which is separated by fractional distillation, are obtained. 61.5 g (which corresponds to a yield of 54%, based on the hydrogen fluoride employed) of 1-trichloromethyl-3-trifluoromethyl-2-chlorobenzene with a melting point of 32°–3° C are obtained at 134° C and under 15 bars.

Analysis of the reaction mixture by gas chromatography gives the following composition:
a. 15.1% of 1,3-bis-(trichloromethyl)-2-chlorobenzene,
b. 5.5% of 1-trichloromethyl-3-(dichloro-fluoromethyl)-2-chlorobenzene,
c. 9.1% of 1-trichloromethyl-3-(chloro-difluoromethyl)-2-chlorobenzene,
d. 36.9% of 1-trichloromethyl-3-(trifluoromethyl)-2-chlorobenzene,
e. 8.0% of 1-(dichloro-fluoromethyl)-3-trifluoromethyl-2-chlorobenzene,
f. 11.0% of 1-(chloro-difluoromethyl)-3-trifluoromethyl-2-chlorobenzene and
g. 4.7% of 1,3-bis-(trifluoromethyl)-2-chlorobenzene.

EXAMPLE 5

470 g of 1,4-bis-(trichloromethyl)-benzene, 2.35 g of antimony pentachloride and 90 g of anhydrous hydrogen fluoride are initially introduced into an autoclave. The autoclave is closed, nitrogen is introduced, as the blanketing gas, under a pressure of 1.5 bars and the mixture is then warmed. The reaction already starts at 30° to 35° C and the hydrogen chloride pressure in the reactor rises to 25 bars. The pressure is kept at this value by letting down. The mixture is warmed up to 70° C and kept at this temperature for 1 hour.

The reaction temperature is then lowered to 40° C and the mixture is stirred for a further 5 hours at the same temperature.

After the end of the reaction, the mixture is cooled and let down. The reaction mixture is washed with dilute hydrochloric acid and then with water.

Analysis of the reaction product by gas chromatography gives the following composition:
a. 13.5% of 1,4-bis-(trichloromethyl)-benzene,
b. 1.8% of 1-trichloromethyl-4-(dichloro-fluoromethyl)-benzene,
c. 3.2% of 1-trichloromethyl-4-(chloro-difluoromethyl)-benzene,
d. 60.7% of 1-trichloromethyl-4-(trifluoromethyl)-benzene,
e. 4.9% of 1-(dichloro-fluoromethyl)-4-trifluoromethyl-benzene,
f. 7.1% of 1-(chloro-difluoromethyl)-4-trifluoromethyl-benzene and
g. 6.5% of 1,4-bis-(trifluoromethyl)-benzene.

234 g (which corresponds to a yield of 59%, based on the hydrogen fluoride employed) of 1-trichloromethyl-4-trifluoromethyl-benzene (boiling point 87°/11 mm, $n_D^{20}$: 1.4896) are obtained by fractional distillation of the reaction mixture.

EXAMPLE 6

174 g of 2,5-bis-(trichloromethyl)-chlorobenzene, 1.74 g of antimony pentachloride and 20 g of anhydrous hydrogen fluoride are initially introduced into an autoclave. The fluorination reaction is carried out in the course of 2 hours at 80° C. During the reaction the pressure rises to 14 bars and is kept at this value by means of a valve.

After the end of the reaction, the mixture is cooled and let down. The reaction mixture is washed with dilute hydrochloric acid and then with water.

Analysis by gas chromatography gives the following composition:
a. 11.9% of 2,5-bis-(trichloromethyl)-chlorobenzene,
b. 8.5% of 2-trichloromethyl-5-(dichloro-fluoromethyl)-chlorobenzene,
c. 29.3% of 2-trichloromethyl-5-(chloro-difluoromethyl)-chlorobenzene,
d. 36.3% of 2-trichloromethyl-5-trifluoromethyl-chlorobenzene,
e. 3.4% of 2-(dichloro-fluoromethyl)-5-trifluoromethyl-chlorobenzene,
f. 4.1% of 2-(chloro-difluoromethyl)-5-trifluoromethyl-chlorobenzene and
g. 0.5% of 2,5-bis-(trifluoromethyl)-chlorobenzene.

52.5 g of 2-trichloromethyl-5-trifluoromethyl-chlorobenzene, which has a boiling point of 118°/14 mm Hg, a $n_D^{20}$ of 1.511 and a purity of about 90%, are obtained by fractional distillation. (10% of isomeric 2-trifluoromethyl-5-trichloromethyl-chlorobenzene).

EXAMPLE 7

4 kg of 1,3-bis-(trichloromethyl)-benzene and 40 g of aluminium chloride are initially introduced into a 5 liter autoclave and reacted with 767 g of anhydrous hydrogen fluoride (which corresponds to 3 mols of hydrogen fluoride per mol of 1,3-bis-(trichloromethyl)-benzene) at a temperature of 70° to 100° C in the course of 4 hours. The hydrogen chloride formed is let down continuously at 20 atmospheres gauge.

The mixture is then cooled and let down.

After adding a further 100 g of aluminium chloride and after increasing the hydrogen chloride pressure to 20 atmospheres gauge, the reaction mixture is stirred for 4 hours at 80° C. It is then cooled, let down and filtered.

According to gas chromatography, the reaction product has the following composition:
a. 38.1% of 1,3-bis-(trichloromethyl)-benzene,
b. 5.5% of 1-trichloromethyl-3-(dichloro-fluoromethyl)-benzene,
c. 4.9% of 1-trichloromethyl-3-(chlorodifluoromethyl)-benzene,
d. 34.9% of 1-trichloromethyl-3-trifluoromethyl-benzene,
e. 2.4% of 1-(dichloro-fluoromethyl)-3-trifluoromethyl-benzene,
f. 1.7% of 1-(chloro-difluoromethyl)-3-trifluoromethyl-benzene and
g. 8.8% of 1,3-bis-(trifluoromethyl)-benzene.

EXAMPLES 8A and 8B

Comparison between a reaction of 1,3-bis-(trichloromethyl)-benzene with hydrogen fluoride without a catalyst and with a catalyst.

1,3-Bis-(trichloromethyl)-benzene is reacted with anhydrous hydrogen fluoride in a molar ratio of 1:2 and under a pressure of 25 bars under the reaction conditions indicated in Table 1.

After the end of the reaction, the mixture is cooled and let down. The reaction mixture is washed with dilute hydrochloric acid and with water.

Analysis, by gas chromatography, of the reaction products prepared under various reaction conditions gives the compositions indicated in Table 1.

Table 1

Composition of the reaction mixture

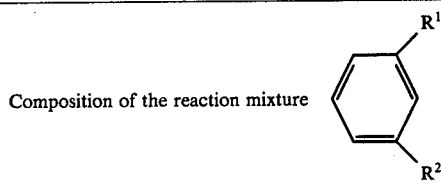

| Catalyst/ Example No. | Temperature, °C | Reaction time, minutes | Number of fluorine atoms 0 | 1 | 2 | 2 | 3 | 3 | 4 | 4 | 5 | 6 |
|---|---|---|---|---|---|---|---|---|---|---|---|---|
| | | | R¹ = CCl₃<br>R² = CCl₃ | CCl₂F<br>CCl₃ | CClF₂<br>CCl₃ | CCl₂F<br>CCl₂F | CF₃<br>CCl₃ | CClF₂<br>CCl₂F | CF₃<br>CCl₂F | CClF₂<br>CClF₂ | CF₃<br>CClF₂ | CF₃<br>CF₃ |
| without | 50 | 120 | 10.1 | 35.9 | — | 34.9 | — | 12.0 | — | 2.8 | — | — |
| Example 8A | 75 | 60 | 4.3 | 31.3 | — | 48.0 | — | 10.1 | — | 1.9 | — | — |
| Example 8A | 100 | 30 | 4.5 | 33.3 | — | 47.6 | — | 8.8 | — | 2.5 | 0.2 | — |
| 1% by weight of SbCl₅ Example 8B | 60 | 120 | 39.0 | 2.7 | 2.3 | — | 47.4 | — | 1.6 | — | 1.6 | 2.9 |

A comparison of the reaction of bis-(trichloromethyl)-benzenes with hydrogen fluoride without a catalyst and with a catalyst shows that the catalytic reaction has the following advantages:

a. In the reaction without a catalyst a statistical distribution of the fluorine atoms takes place, whilst in the reaction with a catalyst trichloromethyl-trifluoromethyl-benzene is formed preferentially.

b. In the non-catalytic reaction the fluorine atoms distribute themselves between the two methyl groups in the compound which contains three fluorine atoms and three chlorine atoms. In contrast, the trifluoromethyl-trichloromethyl isomer is formed exclusively in the catalytic reaction according to the process of the invention.

EXAMPLE 9

175 g of 1,3-difluoro-4,6-bis-(trichloromethyl)-benzene, 1.75 g of antimony pentafluoride and 30 g of anhydrous hydrogen fluoride are initially introduced into an autoclave. The autoclave is closed, nitrogen is introduced, as a blanketing gas, under a pressure of 2 bars and the mixture is then warmed up to 80° C. After this temperature has been reached, the stirrer is switched on and the hydrogen chloride which is liberated during the fluorination is let down at 18 bars by means of a valve. After one hour the chlorine/fluorine exchange has ended. The mixture is stirred for a further 4 hours at 80° C, then cooled and let down and the liquid residue is washed with dilute aqueous hydrochloric acid and then with water.

142 g of a crude product ($n_D^{20}$: 1.4739) of the formula

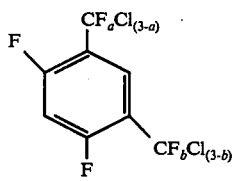

are obtained.

Analysis by gas chromatography gave the following composition for the crude product:

| a+b (number of fluorine atoms in the side chains) | 0 | 1 | 2 | 3 | 4 | 5 | 6 |
|---|---|---|---|---|---|---|---|
| Proportion in % | 13.5 | 3.9 | 6.4 | 50.9 | 7.6 | 9.8 | 7.2 |

By means of fractional distillation, 1,3-difluoro-4-trifluoromethyl-6-trichloromethyl-benzene is obtained, as a water-white liquid ($n_D^{20}$: 1.4712) and, according to analysis by gas chromatography, in a purity of 95.2%, at a boiling point of 86° C/11 mm Hg, from the crude product.

a. Preparation of 1,3-difluoro-4,6-bis-(trichloromethyl)-benzene 1.8 l of anhydrous hydrogen fluoride are initially introduced into a stirred vessel made of stainless steel and 625 g of 1,3-dimethyl-4-fluoro-aniline (see Am. Soc. 54, 2981) are introduced, whilst cooling. Subsequently, a diazotisation reaction is carried out, at 0° C, by adding 374 g of sodium nitrite in portions. The mixture is then slowly heated to room temperature. Since the splitting of the diazonium fluoride proceeds only slowly at this temperature, the temperature is raised up to the reflux temperature for hydrogen fluoride. Towards the end of the reaction 800 ml of dimethylsulphoxide are added and the temperature is further raised to 80° C and this temperature is maintained for 30 minutes. Subsequently, the reaction mixture is poured onto ice and extracted with methylene chloride and the organic phase is separated off, dried over sodium sulphate and then distilled. 428 g of 1,3-difluoro-4,6-dimethylbenzene with a boiling point of 143° C and a melting point of 30° to 31° C are obtained.

735 g of the 1,3-difluoro-4,6-dimethylbenzene prepared as described above are treated with chlorine gas, whilst irradiating with UV light and whilst slowly heating in the temperature range of 110° to 190° C, until no further absorption of chlorine takes place.

1,516 g of 1,3-difluoro-4,6-bis-(trichloromethyl)-benzene with a boiling point of 156° C/12 mm Hg and a melting point of 77° to 79° C are obtained by distilling the reaction product under reduced pressure.

What is claimed is:

1. A process for the preparation of a trichloromethyl-trifluoromethylbenzene of the formula

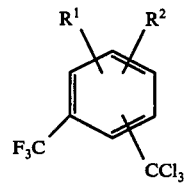

wherein $R^1$ and $R^2$ are independently selected from the group consisting of hydrogen, fluorine, chlorine and bromine which comprises contacting a bis-(trichloromethyl)-benzene of the formula

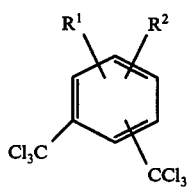

wherein $R^1$ and $R^2$ have the previously assigned significance with less than 6 mols of anhydrous hydrogen fluoride per mol bis-(trichloromethyl)-benzene in the presence of a halogen transfer catalyst.

2. A process according to claim 1 wherein the halogen transfer catalyst is present in the reaction mixture in an amount of 0.1 to 5% by weight.

3. A process according to claim 2 wherein the halogen transfer catalyst is selected from the group consisting of iron trichloride, titanium tetrachloride, aluminum chloride and an antimony-V halide.

4. A process according to claim 3 wherein the halogen transfer catalyst is selected from the group consisting of antimony pentachloride, antimony pentafluoride and antimony-V chloride-fluoride.

5. A process according to claim 4 wherein the catalyst is employed in an amount of 0.1 to 1% by weight.

6. A process according to claim 5 wherein the catalyst is employed in an amount of 0.25 to 0.75% by weight.

7. A process according to claim 2 wherein the reaction is conducted at a temperature of 0° to 150° C.

8. A process according to claim 7 wherein the reaction is carried out at a pressure in the range of from 1 to 50 bars.

9. A process according to claim 8 wherein the process is conducted at a pressure of 20–30 bars.

10. A process according to claim 8 wherein the process is conducted in a sealed vessel at autogenous pressure.

11. A process according to claim 7 wherein the reaction is conducted at a temperature between 40° and 100° C.

12. A process according to claim 11 wherein the process is carried out at a temperature of 50° to 80° C.

13. A process according to claim 2 wherein the halogen transfer catalyst is present in the reaction mixture in an amount of 0.5 to 3% by weight.

14. A process according to claim 7 wherein the reaction is carried out at normal pressure.

15. A process according to claim 1 wherein the process is conducted as a one-step process.

16. A process according to claim 1 wherein the hydrogen fluoride is employed in an amount of 1.5 to 3 mols per mol of bis-(trichloromethyl)-benzene.

* * * * *